United States Patent
Wu et al.

(10) Patent No.: US 8,883,167 B2
(45) Date of Patent: *Nov. 11, 2014

(54) **ETHANOL EXTRACT OF *ANTRODIA CAMPHORATA* FOR INDUCING APOPTOSIS AND PREPARATION METHOD THEREOF**

(75) Inventors: Yang-Chang Wu, Kaohsiung (TW); Mei-Chin Lu, Pingtung County (TW); Fang-Rong Chang, Kaohsiung (TW); Ying-Chi Du, Chiayi (TW); Tung-Ying Wu, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/398,368

(22) Filed: Feb. 16, 2012

(65) Prior Publication Data
US 2012/0141524 A1 Jun. 7, 2012

Related U.S. Application Data

(62) Division of application No. 12/538,549, filed on Aug. 10, 2009, now abandoned.

(30) Foreign Application Priority Data

Feb. 13, 2009 (TW) .............................. 98104772 A

(51) Int. Cl.
*A61K 36/07* (2006.01)
(52) U.S. Cl.
CPC ..................................... *A61K 36/07* (2013.01)
USPC .................................................. 424/195.15
(58) Field of Classification Search
None
See application file for complete search history.

(56) References Cited

U.S. PATENT DOCUMENTS

| | | | |
|---|---|---|---|
| 5,670,673 A * | 9/1997 | Rao | 549/510 |
| 2002/0076457 A1* | 6/2002 | Aylward | 424/779 |
| 2004/0052879 A1* | 3/2004 | Ravagnan et al. | 424/762 |
| 2004/0260105 A1* | 12/2004 | Herold et al. | 554/8 |
| 2007/0219141 A1* | 9/2007 | Jones et al. | 514/22 |
| 2010/0210869 A1 | 8/2010 | Wu et al. | |

FOREIGN PATENT DOCUMENTS

| TW | 591110 | 6/2004 |
|---|---|---|
| TW | I279439 | 4/2007 |
| TW | I299665 | 8/2008 |

OTHER PUBLICATIONS

"Evaluation of the Anti-Inflammatory Activity of Zhankuic Acids Isolated from the Fruiting Bodies of *Antrodia camphorata*" by Shen et al., Planta Med. 70, 310-14 (2004).*

(Continued)

*Primary Examiner* — Theodore R West
(74) *Attorney, Agent, or Firm* — Volpe and Koenig, P.C.

(57) ABSTRACT

A preparation method for an ethanol extract of the fruiting body of *Antrodia camphorata* (EEAC) is provided. The preparation method includes steps of: (a) providing the fruiting body of *A. camphorata* (AC); (b) extracting the fruiting bodies with a first ethanol solution; and (c) obtaining EEAC. EEAC further can be sequentially extracted or fractioned by n-hexane, ethyl acetate and ethanol, and an n-hexane fraction (FC), an ethyl acetate fraction (FA) and an ethanol fraction (FB) respectively are generated. The growth inhibition and apoptosis induction of leukemia cell line HL 60 are effectively mediated by FA product, in which zhankuic acid A is the bioactive marker. The amount of triterpenoid in the fruiting body of AC can be determined by NMR and HPLC analysis.

17 Claims, 13 Drawing Sheets

(56) References Cited

OTHER PUBLICATIONS

Chen et al., "New steroid acids from *Antrodia cinnamomea*, a fungal parasite of *Cinnamomum micranthum*," J. Nat. Prod., (1995), 58(11): 1655-1661.

Chen et al., "Unique formosan mushroom *Antrodia camphorata* differentially inhibits androgen-responsive LNCaP and-independent PC-3 prostate cancer cells," Nutr. Cancer (2007), 57(1): 111-121.

Cherng et al., "Three new triterpenoids from C. *Antrodia cinnamomea*," J. Nat. Prod. (1995), 58(3): 365-371.

Hsu et al., "*Antrodia cinnamomea* fruiting bodies extract suppresses the invasive potential of human liver cancer cell line PLC/PRF/5 through inhibition of nuclear factor kB pathway," Food Chem. Toxicol., (2007), 45(7): 1249-1257.

Hsu et al., "Apoptotic effects of extract from *Antrodia camphorata* fruiting bodies in human hepatocellular carcinoma cell lines," Cancer Lett. (2005), 221(1): 77-89.

Liu et al., "Antihypertensive activities of a solid-state culture of *Taiwanofungus camphoratus* (Chang-chih) in spontaneously hypertensive rats," Biosci. Biotechnol. Biochem. (2007), 71(1): 23-30.

Lu et al., "Induction of G2/M phase arrest by squamocin in chronic myeloid leukemia (K562) cells," Life Sci. (2006), 78 (20): 2378-2383.

Peng et al., "*Antrodia camphorata* extract induces replicative senescence in superficial TCC, and inhibits the absolute migration capability in invasive bladder carcinoma cells," J. Ethnopharmacol (2007), 109(1): 93-103.

Schwab et al., "Involvement of different nuclear hormone receptors in butyrate-mediated inhibition of inducible NFkB signalling," Mol. Immunol., (2007), 44(15): 3625-3632.

Shen et al., "New ergostane and lanostane from *Antrodia Camphorata*," J. Chin. Med., (2003), 14(4): 247-258.

Shetty et al., Transcription factor NF-kB differentially regulates death receptor 5 expression involving histone deacetylase 1, Mol. cell. Biol., (2005), 25(13): 5404-5416.

Song et al., "*Antrodia camphorata* in Submerged culture induce apoptosis of human hepatoma HepG2 cells possibly through regulation of Fas pathway," J. Agric. Food Chem., (2005), 53(14): 5559-5564.

Swarup et al., "Tumor necrosis factor receptor-1-induced neuronal death by TRADD contributes to the pathogenesis of Japanese encephalitis," J. Neurochem., (2007), 103(2): 771-783.

Taplick et al., "Histone H4 acetylation during interleukin0-2 stimulation of mouse T cells," FEBS Lett., (1998), 436(3): 349-352.

Vandergeeten et al., "HIV-1 protease inhibitors do not interfere with provirus transcription and host cell apoptosis induced by combined treatment TNF-a+TSA," Biochem. Pharmacol., (2007), 73(11): 1738-1748.

Wu et al., "Proteomic analysis of the effect of *Antrodia camphorata* extract on human lung cancer A549 cell," Proteomics, (2006), 6(3): 826-835.

Yang et al., "Steroids and triterpenoids of *Antodia cinnamomea*—a fungus parasitic on *Cinnamomum micranthum*," Phytochemistry, (1996), 41(5): 1389-1392.

Lu et al., "Active extracts of wild fruiting bodies of *Antrodia camphorata* (EEAC) induce leukemia HL 60 cells apoptosis partially through histone hypoacetylation and synergistically promote anticancer effects of thrichostatin," A. Arch. Toxicol., (2009), 83(2): 121-129. (online published on Aug. 16, 2008 and published on Feb. 13, 2009).

\* cited by examiner

SEQUENCE LISTING

```
<160> NUMBER OF SEQ ID NOS: 1

<210> SEQ ID NO 1
<211> LENGTH: 10
<212> TYPE: DNA
<213> ORGANISM: Artificial
<220> FEATURE:
<223> OTHER INFORMATION: NFKappaB consensus Oligonucleotide
<301> AUTHORS: Mei-Chin Lu, Ying-Chi Du, Jiunn-Jye Chuu, Shiuh-Lin
       Hwang, Pao-Chuan Hsieh, Chih-Sheng Huang, Fang-Rong Chang,
       Yang-Chang Wu
<302> TITLE: Active extracts of wild fruiting bodies of Antrodia
       camphorata (EEAC) induce leukemia HL 60 cells apoptosis partially
       through histone hypoacetylation and synergistically promote
       anticancer effect of trichostatin A
<303> JOURNAL: Archives of Toxicology
<304> VOLUME: 83
<305> ISSUE: 2
<306> PAGES: 121-129
<307> DATE: 2009-02-28

<400> SEQUENCE: 1
gggactttcc                                                              10
```

ETHANOL EXTRACT OF *ANTRODIA CAMPHORATA* FOR INDUCING APOPTOSIS AND PREPARATION METHOD THEREOF

CROSS REFERENCES TO RELATED APPLICATIONS

This application is a division of and is based upon and claims the benefit of priority for U.S. application Ser. No. 12/538,549, filed on Aug. 10, 2009, and claims the benefit of priority from Taiwan Patent Application No. 098104772, filed on Feb. 13, 2009, in the Taiwan Intellectual Property Office, the disclosures of which are incorporated herein in their entirety by reference.

FIELD OF THE INVENTION

The present invention relates to an extract of the fruiting body of *Antrodia camphorata* (AC) and the preparation method thereof. In particular, the present invention related to an ethanol extract of the fruiting body of *A. camphorata* (abbreviated as EEAC) and the preparation method thereof EEAC can effectively induce cancer apoptosis. Further, the organic solvent extracts are obtained after EEAC is extracted with organic solvents of increasing polarities and can effectively inhibit proliferation, induce cancer cells to enter cell death and apoptosis program.

BACKGROUND OF THE INVENTION

*Antrodia camphorata* (AC), by name niu-chang-chih or jang-jy is an endemic fungus in Taiwan and grows in the internal heartwood (or the dark/humid wood surface) of the particular *Cinnamomum kanehirai* in 400 to 2000 meters altitude. Therefore, it is uneasily to find out the wide fruiting body of AC or identify the morphological appearance of this Aphyllophorales fungus. In addition, the price of AC is still high due to their biologically active components having potential pharmaceutical value.

Since the fruiting body of AC cannot be easily found and be artificially cultured, mycelia products of AC are popular in the market and announce to own anticancer activity, reduced treatment-related symptoms and other side effects. In addition, mycelia products of AC have recently been reported to have anti-oxidant, antihypersensitive and immunostimulatory effects (Liu et al., 2007). It has been claimed of these mycelia products that they contain active components similar to the wild fruiting bodies with cytotoxic triterpenes, steroids, as well as immunostimulatory polysaccharides reported previously (Chen et al., 2005; Yang et al., 1996).

Traditionally AC has been used as health food to prevent inflammation, hypertension, itchy skin and liver cancer. Therefore, extracts of mycelia and fruiting body of AC are deemed as a potential chemotherapeutic agent against hepatoma, as well as prostate, bladder, lung cancer cells and so on (Chen et al., 2007; Hsu et al., 2007; Peng et al., 2007; Song et al., 2005; Wu et al., 2006). However, the chemical distribution and pharmacological research of niu-chang-chih products are not clarified up to now.

In addition, Taiwan Patent No. 1299665 discloses the extract of AC and the preparation thereof, in which the mycelia of AC is extracted with ethanol to obtain polysaccharides for inhibiting matrix metalloproteinase activities. However, the extract is not extracted with the fruiting body of AC, and the mycelia product thereof cannot inhibit cancer cell growth. Taiwan Patent No. I279439 discloses that the mycelia of AC is cultured to obtain the cultured products by adjusting pH value of medium. However, there is no extraction method disclosed. Taiwan Patent No. 591110 discloses that γ-aminobutyric acid is extracted from the lyophilized mycelia of AC with water or organic solvents. However, the above-mentioned inventions did not disclose any product of the fruiting body of AC extracted with water or organic solvent, and there is no component for cancer therapy or growth inhibition of cancer cell is identified.

It is therefore attempted by the applicant to deal with the above situation encountered in the prior art.

SUMMARY OF THE INVENTION

To overcome the defect that the effective/uniform anticancer components of AC products cannot be obtained from extraction of the mycelia of AC since the anti-cancer triterpenoid does not exist in the mycelia of AC, in the present invention, the wild fruiting body of AC is extracted with ethanol to obtain the ethanol extract of the fruiting body of *A. camphorata* (EEAC) so as to effectively inhibit growth of leukemia and induce apoptosis. Next, the organic solvent extracts of the fruiting body of AC are obtained by extracting EEAC with the organic solvents of increasing polarities, and zhankuic acid A is identified as the effective anticancer component in the organic solvent extract by high performance liquid chromatography (HPLC) and nuclear magnetic resonance (NMR).

In accordance with the first aspect of the present invention, an ethyl acetate extract of the fruiting body of AC is provided. The ethyl acetate extract includes at least one characteristic of: (a) causing a plurality of methyl signals generated from sterol or triterpene at $\delta_H$ 0.5 to 2 and terminal olefinic protons at $\delta_H$ 4.8 to 5.0 on a first $^1$H NMR spectrum when the ethyl acetate extract is dissolved in a deuterium chloroform ($CDCl_3$); and (b) causing signals of terminal olefinic protons at $\delta_H$ 5.0 to 5.4 on a second $^1$H NMR spectrum when the ethyl acetate extract is dissolved in pyridine-D5 ($C_5D_5N$).

Preferably, the ethyl acetate extract further includes at least one compound being one selected from a group consisting of zhankuic acid A, dehydroeburicoic acid, actcin C and zhankuic acid C.

Preferably, zhankuic acid A has characteristic $^1$H NMR signals of two tertiary methyls ($CH_3$-18 and $CH_3$-19) and terminal olefinic protons ($H_2$-28) in 24-exo-methylene-26-oic acid side-chain, and the ethyl acetate extract further has characteristic signals of triterpenoid the same with those of the zhankuic acid A.

Preferably, the ethyl acetate extract is fractionized from an ethanol extract of the fruiting body of AC.

In accordance with the second aspect of the present invention, a method for measuring an existence and an amount of triterpenoid of a target object is provided. The method includes steps of: (a) extracting the target object with a first ethanol solution to obtain an ethanol extract; (b) sequentially extracting the ethanol extract with n-hexane and ethyl acetate to obtain an ethyl acetate extract; and (c) measuring the existence and the amount of triterpenoid in the ethyl acetate extract.

Preferably, in the step (c), the existence of the triterpenoid is performed is performed by a nuclear magnetic resonance at a resolution of at least 200 MHz, the ethyl acetate extract is dissolved in a pyridine-D5 ($C_5D_5N$), and the amount of the triterpenoid is performed by a high performance liquid chromatography (HPLC).

Preferably, the target object is the fruiting body of AC.

In accordance with the third aspect of the present invention, an extracting method is provided. The method includes steps of: (a) providing the fruiting body of AC; (b) extracting the fruiting body with a first ethanol solution; and (c) obtaining an ethanol extract of the fruiting body.

Preferably, the step (a) further includes a step (a1) of grinding the fruiting body.

Preferably, the step (c) further includes a step (c1) of extracting the ethanol extract with at least one organic solvent to obtain an organic solvent extract.

Preferably, the at least one organic solvent has a total number of species more than one, each of the at least one organic solvent has a polarity, and the step (c1) has a extracting sequence that the polarity of a specific one of the at least one organic solvent is higher than that of a preceding one of the specific organic solvent.

Preferably, the at least one organic solvent is one selected from a group consisting of n-hexane, ethyl acetate, a second ethanol solution and a combination thereof.

Preferably, the step (c1) further includes steps of: (c11) extracting the ethanol extract with n-hexane to obtain an n-hexane extract and a first residue; (c12) extracting the first residue with ethyl acetate to obtain an ethyl acetate extract and a second residue; and (c13) extracting the second residue with a second ethanol solution to obtain a second ethanol extract.

Preferably, the step (c12) further includes a step (c121) of isolating the ethyl acetate extract with a plurality of trichloromethane-methanols to obtain zhankuic acid A, wherein the plurality of trichloromethane-methanols have respective ratios of trichloromethane to methanol.

Preferably, the step (c12) further includes a step (c121) of isolating the ethyl acetate extract with a plurality of n-hexane-ethyl acetate-methanols to obtain a plurality of fractions of the ethyl acetate extract, wherein the plurality of n-hexane-ethyl acetate-methanols have respective ratios of n-hexane-ethyl acetate to methanol.

Preferably, the step (c121) further includes at least one step of: (c121-1) sequentially isolating a first one of the plurality of fractions with ethyl acetate-dichloromethane-methanol, trichloromethane-methanol and methanol-water to obtain dehydroeburicoic acid; (c121-2) sequentially isolating a second one of the plurality of fractions with ethyl acetate-dichloromethane-methanol and acetonitrile-water having a first ratio of acetonitrile to water to obtain zhankuic acid A; (c121-3) sequentially isolating a third one of the plurality of fractions with dichloromethane-methanol and acetonitrile-water having a second ratio of acetonitrile to water to obtain actcin C; and (c121-4) sequentially isolating a fourth one of the plurality of fractions with dichloromethane-methanol and acetonitrile-water having a third ratio of acetonitrile to water to obtain zhankuic acid C.

Preferably, the step (b) further generates a third residue, and the method further includes a step (c1) of extracting the third residue with water to obtain a water extract.

Preferably, the ethanol extract is used to treat a cell for regulating expression of a specific protein of the cell.

Preferably, the cell is a leukemia cell, and the specific protein is one selected from a group consisting of histone, histone deacetylase, histone acetylase, a p21, a poly (ADP-ribose) polymerase (PARP), a Bax, a Bcl-2, a death receptor (DR5), a tumor necrosis factor receptor-associated death domain (TRADD), a p50 and a p65 and a combination thereof.

Preferably, the ethanol extract and 7-[4-(dimethylamino)phenyl]-N-hydroxy-4,6-dimethyl-7-oxohepta-2,4-dienamide (trichostatin A) have a synergistic effect of causing a cell to go into apoptosis.

The above objectives and advantages of the present invention will become more readily apparent to those ordinarily skilled in the art after reviewing the following detailed descriptions and accompanying drawings, in which:

BRIEF DESCRIPTION OF THE DRAWINGS

FIGS. 7(A) and 7(B) respectively are the immunoblotting patterns showing various protein expressions of TSA, EEAC and the combination thereof in HL 60 cells, wherein FIG. 7(A) shows expressions of p21, PARP, Bcl-2 and Bax, and FIG. 7(B) shows expressions of p50, p65, TRADD and DR5;

DETAILED DESCRIPTION OF THE PREFERRED EMBODIMENT

Figure 1:
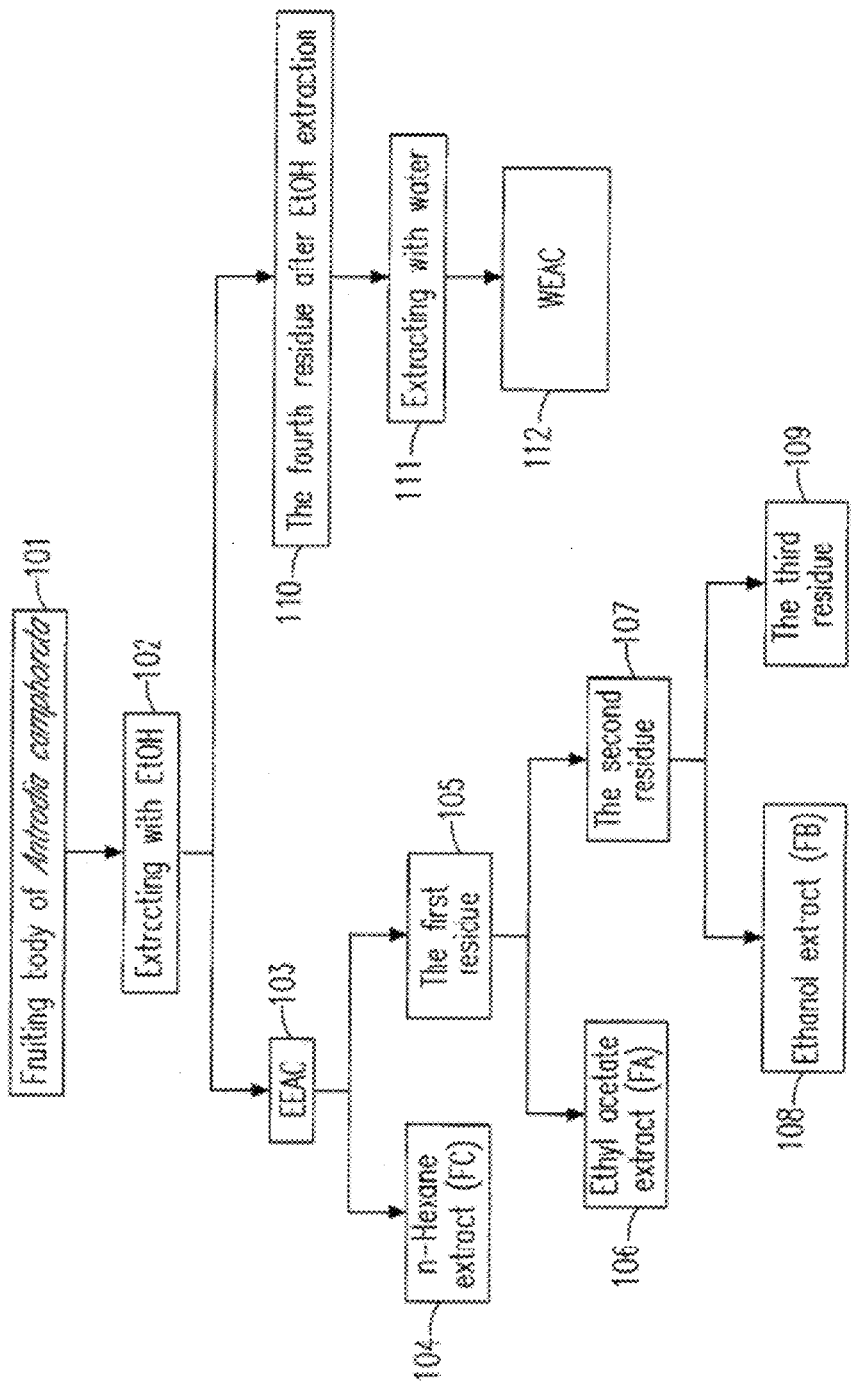
FIG. 1 illustrates the flowchart for preparing EEAC and its organic solvent extracts in the present invention.

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

Embodiment 1

Biological Experiments

Experiment 1

Ethanol Extract and Water Extract Prepared from Fruiting Body of Wild *Antrodia Campharata*

Fifty-two grams (52 g) of the dried fruiting body of AC was ground as fine powder, which was boiled to flux with ethanol at 75° C. at a ratio of 1:10 (w/v) for 2 hours. The extract was cooled and then was allowed to precipitate overnight at 4° C. The supernatant of extract was further filtered by a filter paper, centrifuged at 3,000 rpm for 30 minutes to remove the precipitate, and then the extract was lyophilized and stored at −70° C. This extract is named as "the ethanol extract of the fruiting body of *A. camphorata* (EEAC)". Further, the residue was further boiled to flux at a ratio of 1:10 (w/v) for 6 to 8 hours. The supernatants were filtered and then centrifuged at 3,000 rpm for 30 minutes to remove the precipitate. The product, named as "the water extract of the fruiting body of A. camphorata (WEAC)", was lyophilized and stored at −70° C.

Experiment 2

Further Extraction and Fractionation of EEAC

To identify the biologically active components of EEAC, 1 g of the dried fruiting body of AC was ground and extracted according to the method in Experiment 1. Fifty-percent inhibition concentration ($IC_{50}$) of EEAC was determined as 104.82 µg/ml by MTT (3-(4,5-dimethylthiazol-2-yl)-2,5-diphenyltetrazolium bromide) assay; however, WEAC was inactive ($IC_{50}$>200 µg/ml). EEAC (203.1 mg) was extracted with solvents of increasing polarities (n-hexane, ethyl acetate and ethanol sequentially), and three different extracts, 12.8% (26.0 mg) of n-hexane extract (FC), 61.6% (125.1 mg) of ethyl acetate extract (FA) and 8.4% (17.0 mg) of ethanol extract (FB), and 10.0% (20.2 mg) of the insoluble residue were yielded. Percentage is referred to yields in weight percentage of EEAC, milligram is referred to the corresponding dried weight after fractionation.

Experiment 3

Isolation and Purification of Zhankuic Acid A

EEAC fraction of 95.4 mg was chromatographed using Sephadex LH-20 with trichloromethane-methanol ($CHCl_3$-MeOH) (1:3) to obtain three fractions, wherein Fraction 2 was further separated by preparative thin layer chromatography (TLC) with $CHCl_3$-MeOH (25:1) to obtain 8 sub-fractions. Sub-fraction 2-1 of 10.3 mg was purified using ODS HPLC column (250×10 mm, Hypersil®, MeOH—$H_2O$ (85: 15)) to obtain 4.3 mg of zhankuic acid A (retention time ($R_t$) 10 min, flow rate 2 ml/min).

The equipments for analyzing other physical and chemical characters of zhankuic acid A were used as follows. $^1H$ and $^{13}C$ NMR spectra were recorded on Varian Unity Plus 400, or Varian Gemini 200 NMR spectrometers. Chemical shifts and coupling constants respectively were represented as parts per million (ppm, δ) and Hertz (Hz). LRESIMS (low-resolution electrospray ionization mass spectra) was measured on a VG Biotech Quatro 5022 mass spectrometer. Silicon gel 60 (Merck, 230 to 400 mesh) and Sephadex LH-20 were used for column chromatography, while TLC was carried out on Silica gel $GF_{254}$ pre-coated plates with detection using 50% sulfuric acid followed by heating on the hot plate. HPLC was performed with a Hitachi L-7100 pump and D-7000 interface equipped with a Bischoff RI detector using ODS columns.

Experiment 4

Cell Culture, Cell Viability and Cytotoxicity

Human leukemia HL 60 cell line was purchased from American Type Culture Collection (ATCC, Manassas, Va.) and incubated in RPMI 1640 medium supplemented with 10% fetal calf serum, 2 mM glutamine, 100 units/ml penicillin and 100 µg/ml streptomycin at 37° C. in a humidified atmosphere of 5% carbon dioxide.

Cell viability was determined by the trypan blue dye exclusion and cytotoxicity was assessed by MTT assay. First, 1×10$^5$ HL 60 cells were plated in 96-well plates and treated with different concentrations of EEAC dissolved in dimethyl sulfoxide (DMSO) at the concentrations of 0 to 150 µg/ml for 24 hours. Death cells then were stained with trypan blue, and the survival cells were calculated with hemocytometer. In MTT assay, 1.2 mg/ml MTT was added in each well, which was incubated for 2 hours to form crystal violet, formazan. Formazan was dissolved in DMSO, and absorbance was detected at a wavelength of 570 nm.

Experiment 5

Flow Cytometry

HL 60 cells (1×10$^6$) were incubated in the 10-cm dish and treated with known concentrations of EEAC for 24 hours. The treated cells were washed with ice-cold phosphate-buffered saline (PBS) twice and harvested by centrifuging at 37° C. at 200×g for 5 minutes. Cells were fixed with 70% (v/v) ethanol at 37° C. for 30 minutes, and then were resuspended in 1 ml propidium iodium (PI) reagent (containing 0.1% Triton X-100, 100 µg/ml ribonuclease (RNase) A and 500 µg/ml PI) at 37° C. for 30 minutes. The cells were detected with the flow cytometer, and data were analyzed with FACScan and Cell Quest Program (Becton Dickinson).

Experiment 6

Evaluation of DNA Fragmentation

In this experiment, DNA fragmentation in the apoptotic cells were determined by gel electrophoresis. HL 60 Cells (1×10$^6$) were incubated in the 10-cm dish for 24 hours, then were treated with known concentrations of EEAC (0, 50, 100, 150 and 200 µg/ml respectively) for another 24 hours. Control group was the cells with DMSO treatment. Next, the cells were washed with PBS twice and resuspended in the solution A (containing 10 µM EDTA (2-[2-(bis(carboxymethyl) amino)ethyl-(carboxymethyl)amino]acetic acid), 50 mM Tris-HCl (pH 8.0), 0.5% (v/v) sodium dodecyl sulfate (SDS) and 1 mg/ml proteinase K) at 56° C. for 3 hours. Subsequently, RNase at a final concentration of 50 µg/ml was added therein for reacting 1 hour. Cellular DNA was extracted with phenol/chloroform/isopropanol (25:24:1, v/v), and cellular DNA fragmentation was determined by gel electrophoresis so as to evaluate apoptosis.

Experiment 7

Histone Isolated by Acid Extraction

This experiment was performed in accordance with the literature of Taplick et al. (1998). First, cells were harvested at 700×g, washed with ice-cold PBS once, resuspended in 1 ml lysis buffer (containing 10 mM Tris-HCl (pH 6.5), 50 mM sodium sulfate, 10 mM magnesium chloride, 10 mM sodium butyrate, 8.6% sucrose and 1% Triton X-100) and centrifuged at 1,000×g. After three washes in lysis buffer, pellet was resuspended in a buffer containing 10 mM Tris-HCl (pH 7.4) and 13 mM EDTA. After centrifugation, the cells were resuspended in cold sterile water, and sulfuric acid was added therein to 0.4 N. The cells were centrifuged at 10,000×g for 5 minutes after incubation on ice for 1 hour. Total histones in the supernatant were precipitated overnight with 10× volumes of acetone at −20° C. The precipitated histones were collected by centrifugation, dried and resuspended in distilled water, and the protein content was determined by the Bio-Rad protein assay kit (BioRad Laboratories GmbH, Munchen, Germany).

Experiment 8

Nucleoprotein and Cytoplasmic Protein Extraction

This experiment was performed in accordance with the literature of Vandergeeten et al. (2007). Cells were washed with cold PBS and resuspended in the lysis buffer (containing 10 mM HEPES (4-(2-hydroxyethyl)-1-piperazineethanesulfonic acid)-KOH (pH 7.9), 2 mM magnesium chloride, 0.1 mM EDTA, 10 mM potassium chloride, 0.5% IGEPAL (Sigma, I3021), 1 mM phenylmethanesulfonyl fluoride (PMSF), 1 mM DTT and proteinase inhibitors) on ice for 30 minutes. After centrifugation at 10,000×g for 15 minutes, the supernatant containing nucleoprotein was harvested and stored at −80° C., and the protein concentration of the supernatant was determined.

Experiment 9

Western Immunoblotting

The harvested cells were treated with RIPA lysogenic buffer (containing 1×PBS, 1% Nonidet P-40, 0.5% sodium deoxycholate, 0.1% SDS, 1 mM sodium orthovanadate, 100 μg/ml PMSF and 30 mg/ml aprotinin) for 30 minutes (Lu et al., 2006), and then was centrifuged at 20,000×g for 30 minutes. The protein concentration was determined by BCA protein assay kit (Pierce, Rockford, Ill.). Protein was resolved by 7.5%, 10% or 12% SDS-polyacrylamide gel electrophoresis (PAGE) respectively and transferred onto the PVDF nitrocellulose membrane. Protein expressions were sequentially monitored with primary antibody and horse-radish peroxidase (HRP)-conjugated secondary antibody, and then was developed with enhanced chemical luminescence (ECL). Protein expressions were exposed on X-ray film.

Experiment 10

Nuclear Factor Kappa B (NFκB) Transcriptional Factor Assay

This experiment is to determine the effect of EEAC treatment on NFκB activation by TranAM® transcription factor assay (Active Motif, Tokyo, Japan) (Schwab et al., 2007). First, 7 μg of nuclear extract was added to each well of a 96-well culture plate which was pre-coated with NFκB consensus binding oligonucleotide (SEQ ID NO. 1). After 1 hour of incubation with smooth agitation, wells were washed three times with washes buffer and then incubated with p50 or p65 antibody (dilution 1:1,000) for 1 hour at room temperature. After three successive washings, the wells were incubated with HRP-conjugated secondary antibody (dilution 1:1,000) for 1 hour at room temperature followed by the addition of developing solution. The optical density was determined at 405 nm by keeping the reference wavelength at 655 nm Experiment 11

Statistic Analysis

All data were represented as "mean±standard deviation (SD)". The difference between the experiment and the control was analyzed by t-test, and a probability of p<0.05 was considered significant.

Experimental Results

Please refer to FIG. 1, which illustrates the flowchart for preparing EEAC and its organic-solvent extracts in the present invention. In the preparation method of FIG. 1, the ground fruiting body of AC was extracted with ethanol (Steps 101, 102), and then was filtered and centrifuged to obtain EEAC (Step 103) and the residue of the fruiting body of AC (Step 110). To identify the biologically active components for cytotoxicity in the fruiting body of AC, EEAC was further extracted with the organic solvents of increasing polarity, which were ranked: n-hexane, ethyl acetate and ethanol. The preparation method of the organic solvent extracts of the fruiting body of AC was described as follows. EEAC was extracted with n-hexane to obtain the n-hexane extract (fraction C, FC) (Step 104) and the first residue (Step 105). Next, the first residue was further extracted with ethyl acetate to obtain the ethyl acetate extract (fraction A, FA) (Step 106) and the second residue (step 107). The second residue was further extracted with ethanol solution to obtain the another ethanol extract (fraction B, FB) (step 108) and the third residue (step 109). In addition, the residue (step 110) was further boiled and extracted with water (step 111) to obtain the water extract of the fruiting body of AC (WEAC) (step 112).

Figure 2A:
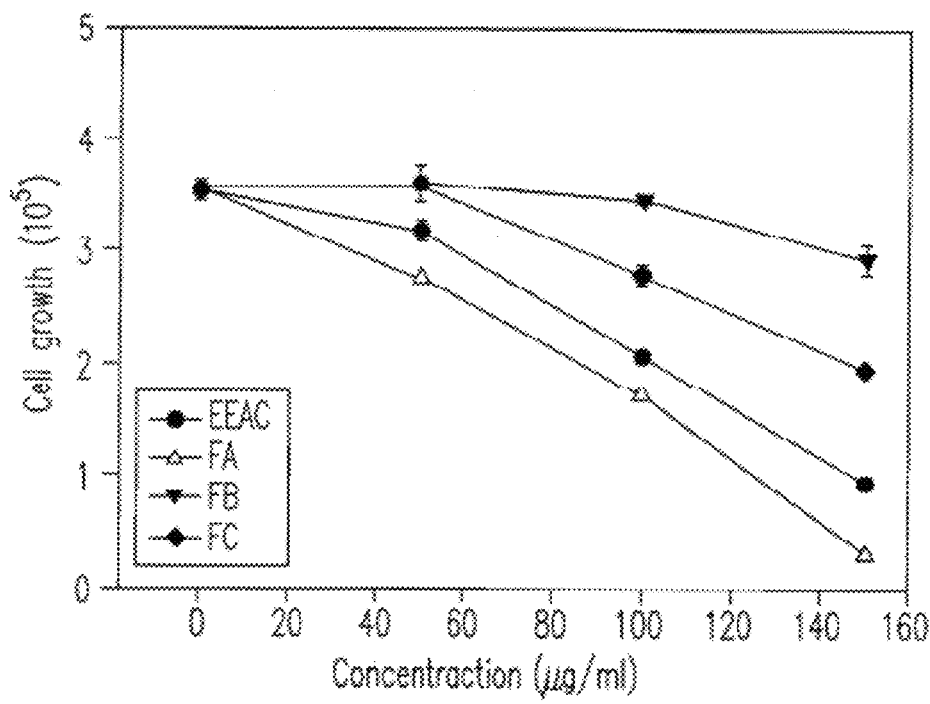
FIG. 2(A) illustrates the growth inhibition of the respective extracts of the fruiting body of AC on HL 60 cells.
Figure 2B:
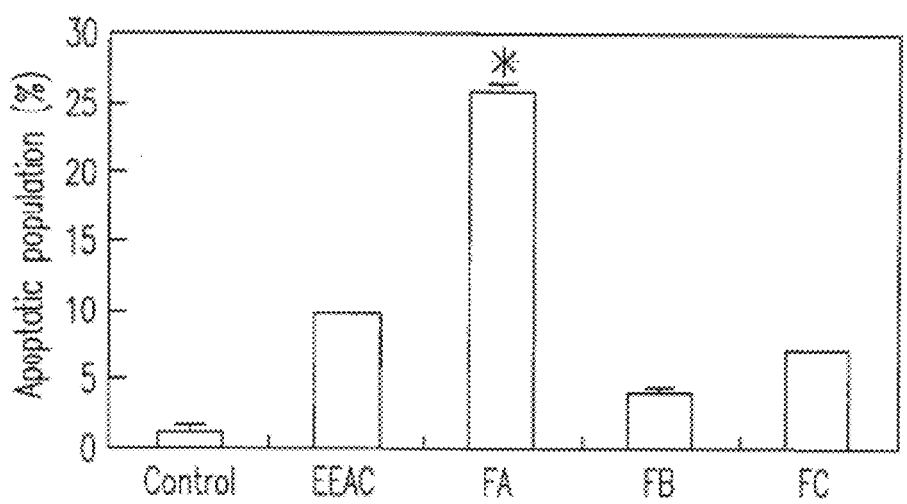
FIG. 2(B) illustrates the apoptosis of HL 60 cells induced by respective extracts of the fruiting body of AC.

To analyze the cytotoxicity of these organic solvents on HL 60 cells, 50% inhibition concentrations ($IC_{50}$) of EEAC and FA respectively on HL 60 cells were determined as 104.82 μg/ml and 80.53 μg/ml by MTT assay, but $IC_{50}$ of FB and FC respectively on HL 60 cells were more than 200 μg/ml. Therefore, FA has better growth inhibition effect on HL 60 cells. Please refer to FIG. 2(A), which illustrates the growth inhibition of the respective extracts of fruiting body of AC on HL 60 cells. In FIG. 2(A), growth inhibition on HL 60 cells was increased with the increasing concentrations of the respective extracts. Please refer to FIG. 2(B), which illustrates the apoptosis of HL 60 cells induced by 100 μg/ml of respective extracts. In FIG. 2(B), comparing with other extracts, FA showed the significant apoptotic ability on HL 60 cells. From the above-mentioned results, it can be known that FA contains the biologically active component for cytotoxicity on HL 60 cells.

Figure 3A:
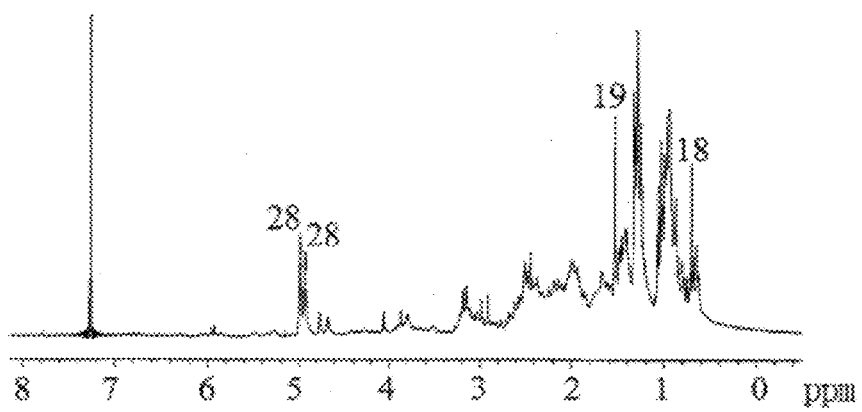
FIG. 3(A) illustrates the $^1$H NMR pattern of the ethyl acetate extract of the fruiting body of AC dissolved in $CDCl_3$.
Figure 3B:
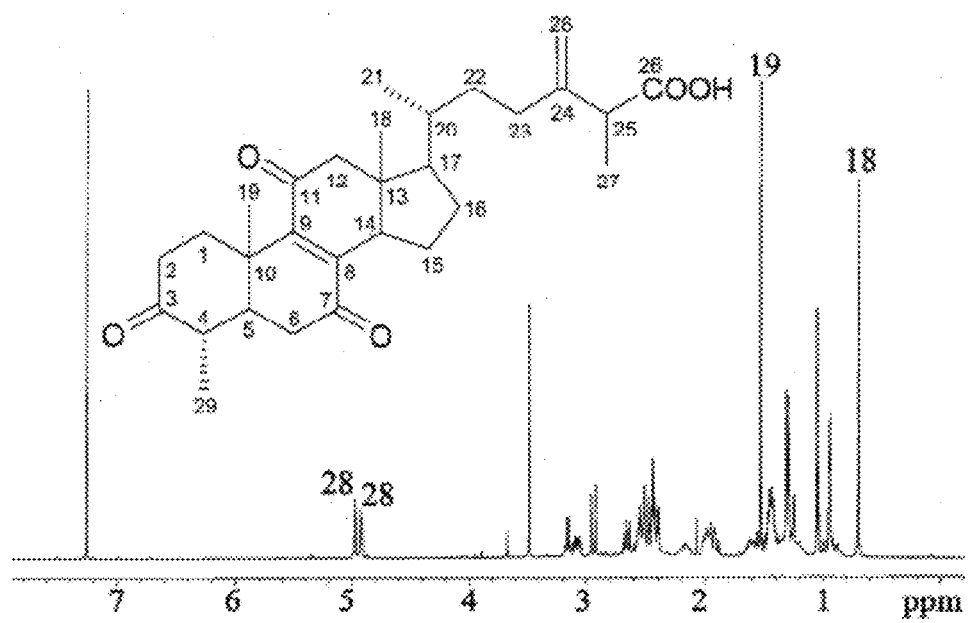
FIG. 3(B) illustrates the $^1$H NMR pattern of zhankuic acid A dissolved in $CDCl_3$.

The $^1$H NMR spectrum of FA was further analyzed. The methyl signals ($CH_3$-18 and $CH_3$-19) of sterol or triterpene was shown at δ0.5 to 2 (FIG. 3(A)) when the NMR profile of FA was 3.0 mg/ml in deuterium chloroform ($CDCl_3$), and the major component of FA was predicted as zhankuic acid A from the spectrum of FIG. 3(A). Further, comparing $^1$H NMR spectrum of FA with that of zhankuic acid A at the same conditions (FIG. 3(B)), it can be found that FA has the similar signals of zhankuic acid A. Characteristic $^1$H NMR signals of zhankuic acid A showed two tertiary methyls ($CH_3$-18 and $CH_3$-19) and terminal olefinic protons ($H_2$-28) in 24-exo-methylene-26-oic acid side-chain, and $^1$H NMR spectrum of the ethyl acetate extract exhibited clearly these distinguishable signals. Therefore, FA indeed is mainly composed of zhankuic acid A which has a chemical formula I as follows.

Formula I

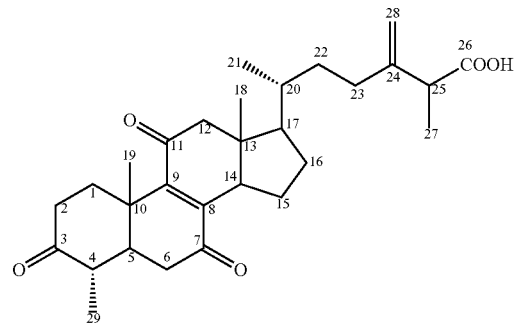

The major component, zhankuic acid A, of FA was a pale-yellow amorphous solid, and its molecular formula was established as $C_{29}H_{40}O_5$ by electrospray ionization mass spectra (ESIMS, m/z 469 [M+H]$^{30}$) and NMR spectra. The most significant signals of its $^1$H NMR spectrum were those corresponding to five methyls (three secondary at δ=0.95, 1.05, 1.30, and two tertiary at δ=0.70, 1.53) and two terminal olefinic methylene protons at δ=4.92 and 4.98. The $^{13}$C NMR spectrum displayed three carbonyl groups ($\delta_C$=200.8, 202.6, and 210.8), four olefinic carbons ($\delta_C$=111.4, 145.5, 148.0, 151.9) and one carboxylic acid ($\delta_C$=178.8). According to the above-mentioned $^1$H NMR analysis, our results suggested that zhankuic acid A was the major component of FA. Moreover, zhankuic acid A exhibited significant cytotoxicity to HL 60 cells ($IC_{50}$ 5.45 μg/ml), and it could serve as a biological marker.

Figure 4:
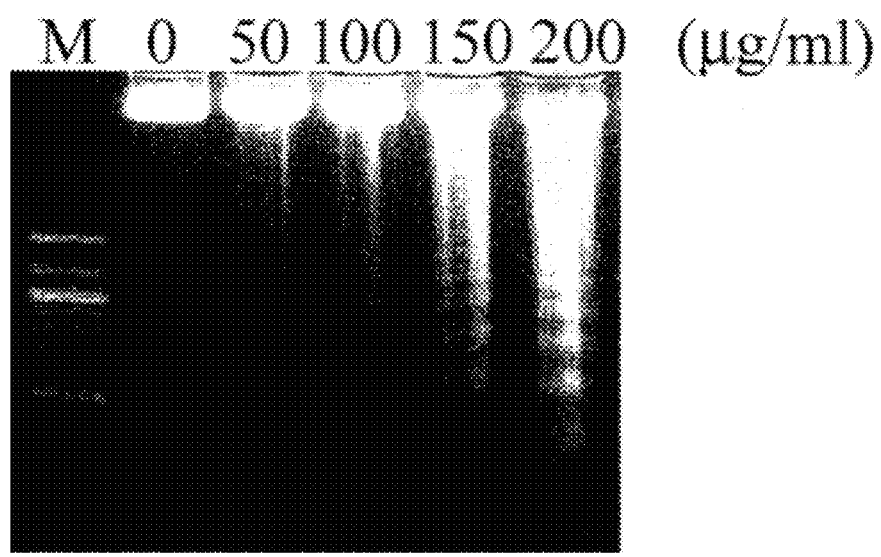
FIG. 4 illustrates the effect of EEAC on DNA fragmentation in HL 60 cells.

Please refer to FIG. 4, which illustrates the effect of EEAV on DNA fragmentation in HL 60 cells. It can be known from FIG. 4 that the concentration of EEAC is proportional to the DNA fragmentation of HL 60 cells, which means EEAC has significant cytotoxicity to HL 60 cells.

Figure 5A:
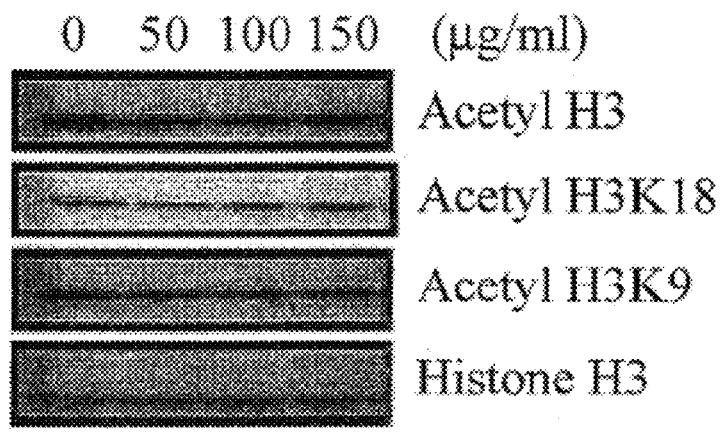
FIG. 5(A) illustrates the immunoblotting patterns showing the effect of EEAC on histone acetylation in HL 60 cells.
Figure 5B:
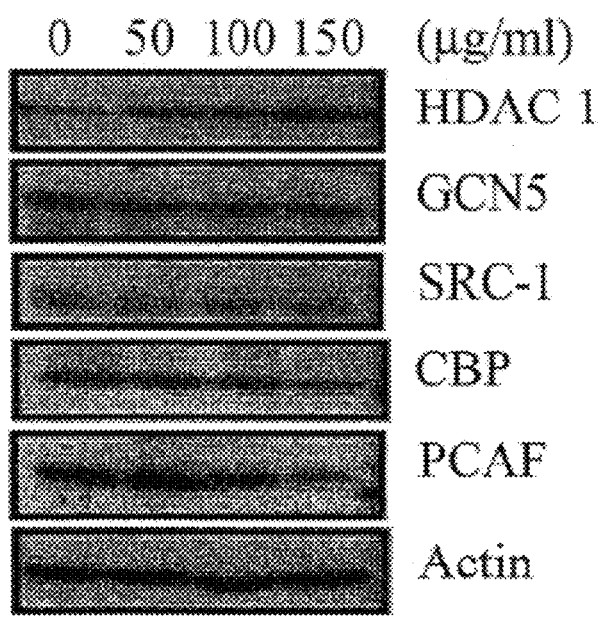
FIG. 5(B) illustrates the immunoblotting patterns showing the activity of the histone acetylation-related enzymes regulated by EEAC in HL 60 cells.

Since chromatin structure can be regulated by histone acetylation and histone deacetylation, histone plays an important role on regulating gene expression, which is accomplished by acetylating specific lysine of histone with histone acetyltransferase (HAT) and deacetylating lysine thereof with histone deacetylase (HDAC). Transcription only can be processed on acetylated chromatin, otherwise, transcription would be ceased. Please refer to FIG. 5(A), which illustrates the immunoblotting patterns showing the effect of EEAC on histone acetylation in HL 60 cells. In FIG. 5(A), EEAC showed the dose-dependent relationship to the low level acetylation of histones (H3, H3K18 and H3K9) in HL 60 cells. Please refer to FIG. 5(B), which illustrates the immunoblotting patterns showing the activity of the histone acetylation-related enzymes regulated by EEAC in HL 60 cells. In FIG. 5(B), deacetylations of histone H3, including inhibition of GCN5, CBP, SRC-1 and PCAF and promotion of HDAC1, were regulated by EEAC with HAT and HDAC.

Figure 6:
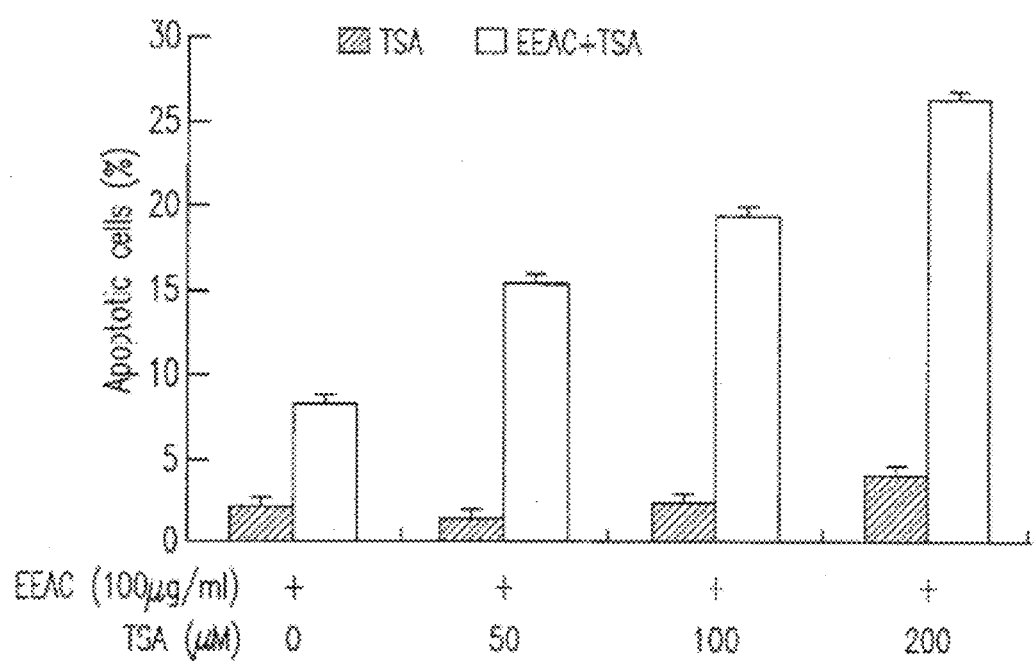
FIG. 6 illustrates the synergistic effect of EEAC and TSA on the survival in HL 60 cells.

Trichostatin A (TSA) is a microbial metabolite, which can promote acetylation of histone H3. Since H3 acetylation is accumulated (hyper-acetylation), trichostatin A can effectively inhibit leukemia proliferation. Please refer to FIG. 6, which illustrates the synergistic effect of EEAC and TSA on the survival in HL 60 cells. In FIG. 6, comparing 100 μg/ml EEAC treatment alone with TSA treatment alone, EEAC had better cytotoxicity effect on HL 60 cells than TSA. Further, the combined treatment of 100 μg/ml EEAC and different dosages of TSA had synergistic effect on HL 60 cells, and the cytotoxicity effect was increased with the increasing TSA dosages.

Figure 7A:
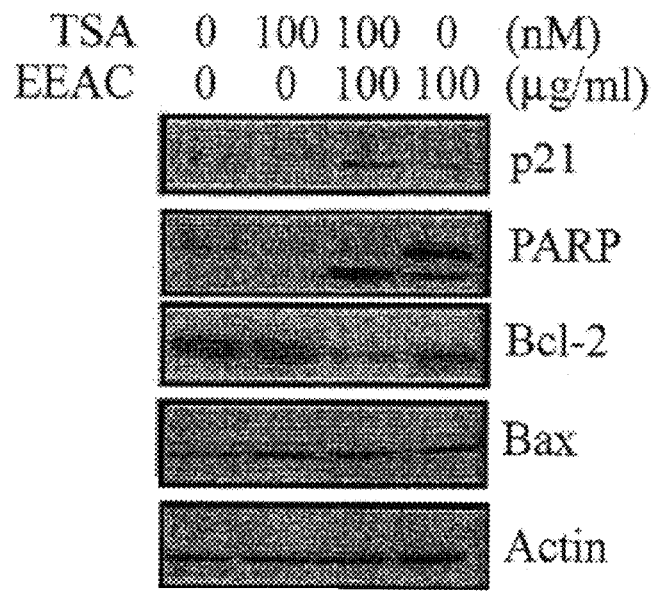
Figure 7B:
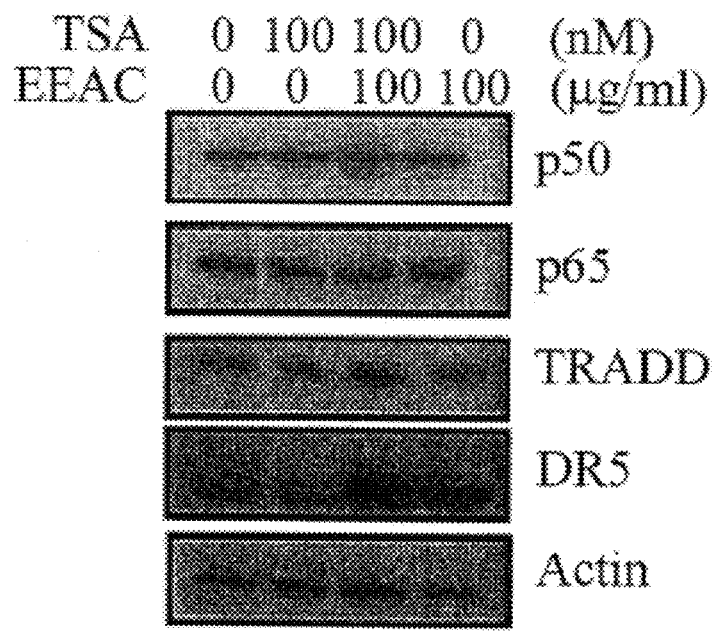

Please refer to FIGS. 7(A) and 7(B), which respectively are the immunoblotting patterns showing various protein expressions of TSA, EEAC and the combination thereof in HL 60 cells. FIG. 7(A) was subjected to p21, PARP, Bcl-2 and Bax which related to growth inhibition and apoptotic induction. It is found that p21 expression of HL 60 cells is increased and Bcl-2 and cleaved PARP expressions thereof are inhibited by cooperatively treating TSA with EEAC.

Since *A. camphorata* is potent FAS (TRAIL)-sensitizing agent in a variety of different TRAIL-resistant human cancer cells (Hsu et al., 2005), DR5 and TRADD interact specifically with death domain of DR4. DR4 activation promotes the binding of TRADD and the subsequent recruitment of DR5 to promote apoptosis (Swamp et al., 2007). When HL 60 cells were individually treated TSA or EEAC or cooperatively treated with TSA and EEAC, it can be found that the immunoblotting analysis for TRADD and DR5 revealed 2 and 4 fold increases over the corresponding control and TSA treatment alone (FIG. 7(B)). It can be known from FIG. 7(B) that the combination-induced upregulation of DR5 is mediated by EEAC, but upregulation of TRADD is mediated synergistically by TSA and EEAC. Therefore, the combined treatment with TSA and EEAC cooperatively targeted the TRAIL pathway.

Certain cancer therapeutic agents induce the expression of DR5 in cancer cells and are thereby able to augment TRAIL-induced apoptosis or initiate apoptosis. Therefore, TRAIL is one of the promising new candidates for cancer therapeutics. In addition, NFκB activation can be triggered by direct stimulation of CD95 and the TRAIL death receptors as well as by overexpression of FLIP protein, and NFκB transcription factor differentially regulated the DR5 expression involving HDAC1 (Shetty et al., 2005). To examine the effect of NFκB activation on cellular apoptosis in response to combined treatment, it is found that the combined treatment significantly increases the translocation of NFκB p65, but does not affect the expression with total extracts of cells. Obviously, combination-induced p65 translocation may be mediated by EEAC treatment alone.

Figure 8:
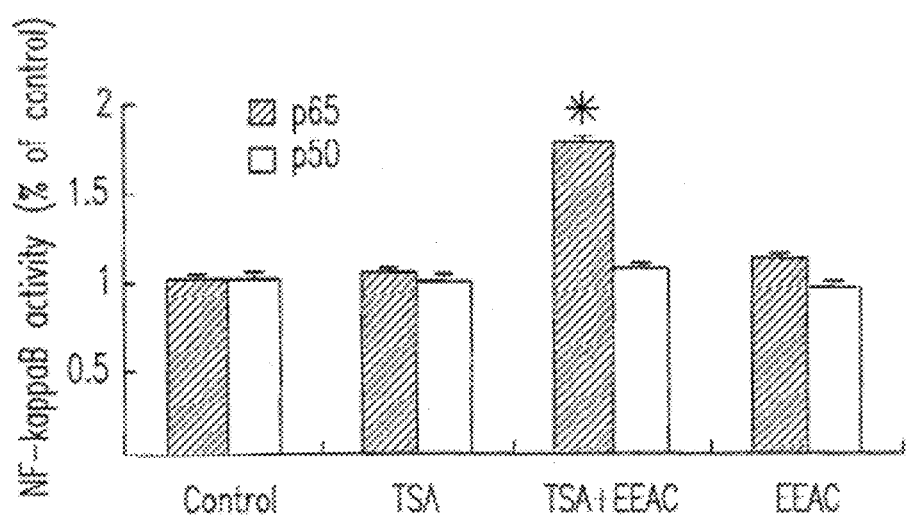
FIG. 8 illustrates the NFκB p65 activity of TSA, EEAC and the combination thereof in HL 60 cells.
Figure 9A:
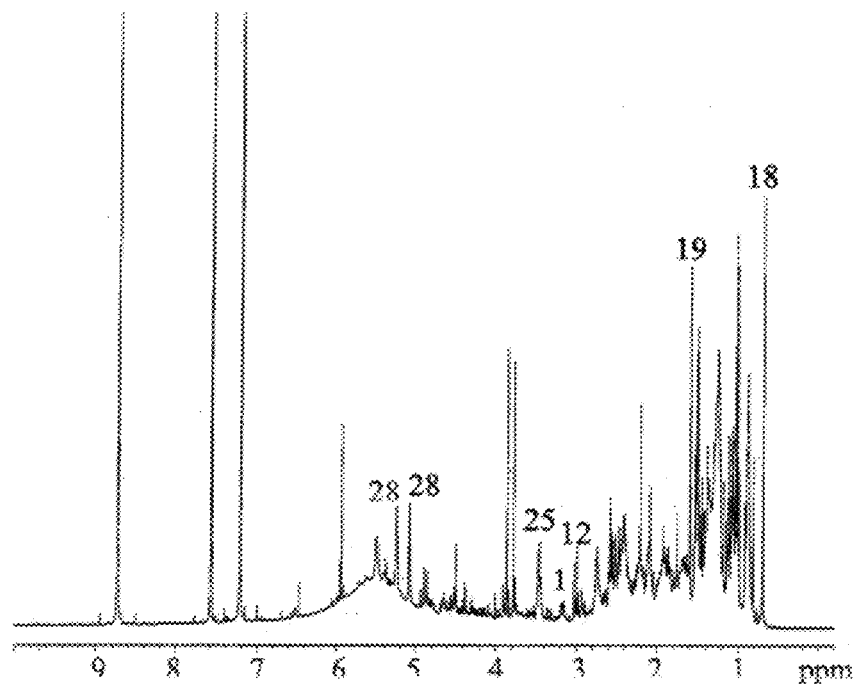
FIGS. 9(A) to 9(E) respectively show $^1$H NMR spectra of (A) EEAC, (B) FC, (C) FA, (D) FB and (E) zhankuic acid A dissolved in $C_5D_5N$ at 400 MHz.
Figure 9B:
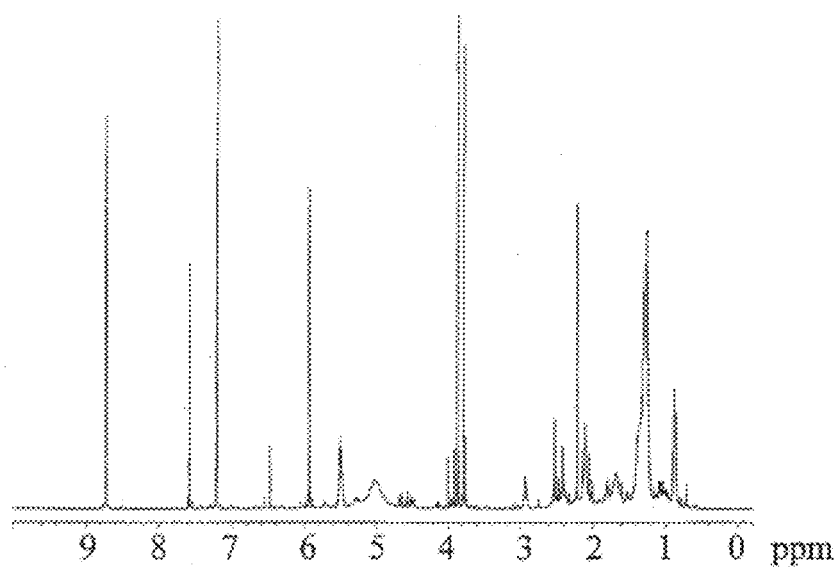
Figure 9C:
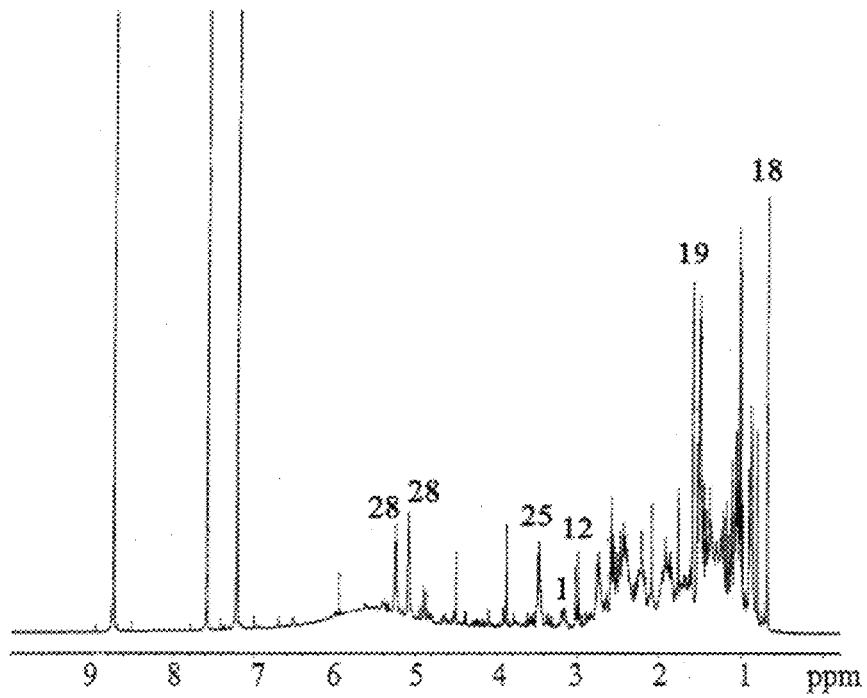
Figure 9D:
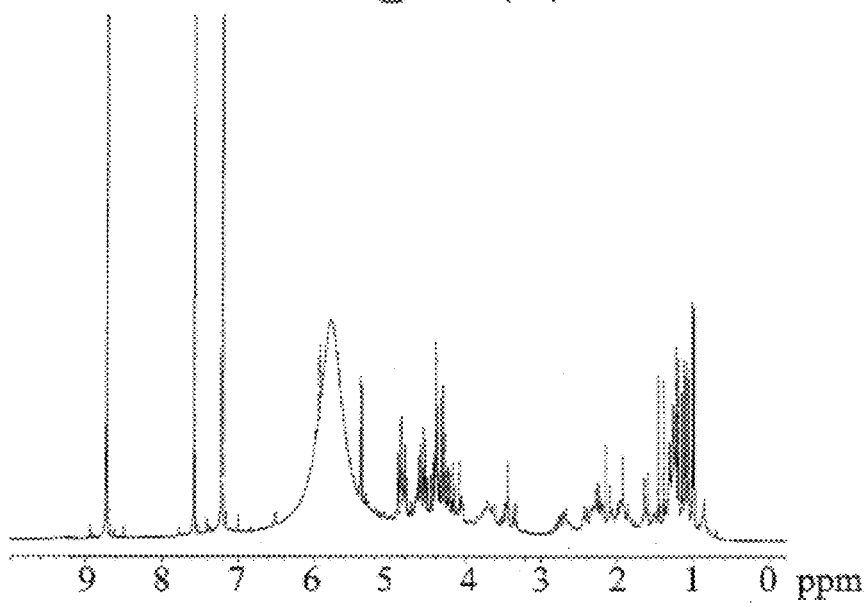
Figure 9E:
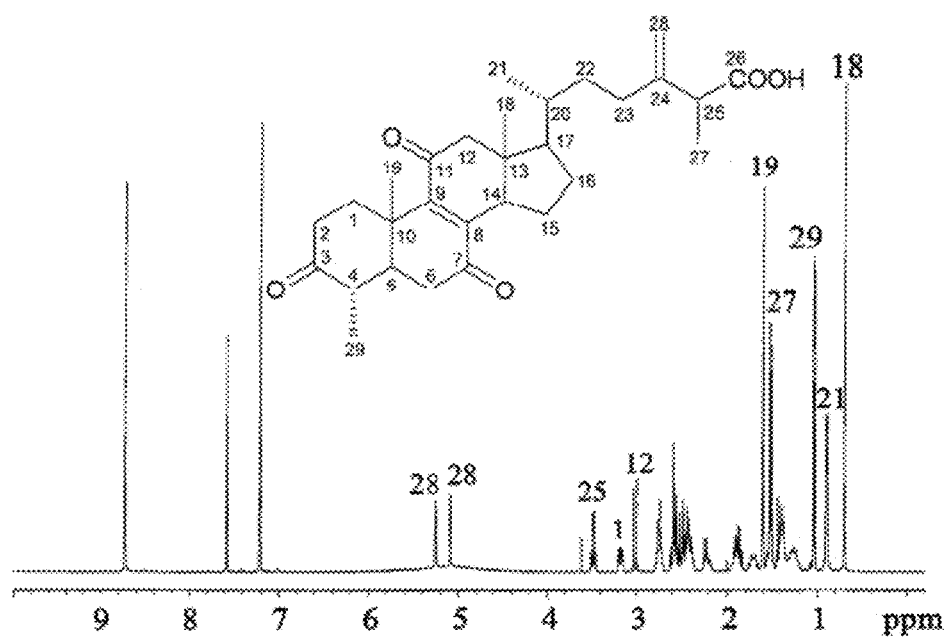

Treatment of HL 60 cells with TSA and EEAC resulted in an increase of basal NFκB p65 DNA binding activity in the nucleus (+78% vs. control, $p<0.05$). In contrast, basal p50 NFκB DNA binding activity was not affected in response to different treatments (FIG. 8), further supporting the suggestion that nuclear translocation of p65 and activation are responsible for the combined treatment-induced NDκB p65 activation.

In the present invention, the obtained EEAC can effectively inhibit growth of HL 60 cells and induce apoptosis mediated histone hypoacetylation and suppression of acetyltransferase activity (including GCN5, CBP and PCAF) in HL 60 cells. In addition, combined treatment of EEAC and TSA on HL 60 cells can synergistically inhibit cellular growth and induce apoptosis.

Zhankuic acid A was identified as the major active component in EEAC after the respective organic solvent extracts obtained by further extracting EEAC with organic solvents and NMR analysis. Accordingly, EEAC can be the potential chemotherapeutic agent.

Embodiment 2

This Embodiment used another fruiting body of AC to prepare 11 g of lyophilized EEAC according to the preparation method in Experiment 1 of Embodiment 1. Subsequently, EEAC was sequentially extracted with n-hexane, ethyl acetate and ethanol according to the method in Experiment 2 of Embodiment 1 to obtain three different extracts, 12.7% (1.4 g) FC, 61.8% (6.8 g) FA and 10.0% (1.1 g) FB, and 5.5% (0.6 g) insoluble residue. Percentage is referred to the weight percentage in EEAC, gram is referred to the dry weight after extraction.

Experiment 1

Anti-Leukemia Activity

To compare with the controls in the prior art, the respective lyophilized EEAC (100 mg) in Embodiment 2 was extracted with three partition extraction methods, and anti-leukemia activity between the respective obtained extracts and the extracts in Embodiment 2 was compared. In Control 1, 101.9 mg lyophilized EEAC was fractionation with ethyl acetate and water (100 ml each, 1:1 (v/v)) by liquid-liquid partition extraction according to the literatures of Chen et al., 1995 and Hsu et al., 2007. The ethyl acetate extract of the fruiting body of AC (FEA-EA, 78.1%, 79.6 mg) and the water extract of the fruiting body of AC (FW-EA, 19.6%, 20.0 mg) were obtained.

In Control 2, 100.3 mg lyophilized EEAC was fractionation with chloroform and water (100 ml each, 1:1 (v/v)) by liquid-liquid partition extraction according to the literature of Cherng et al., 1995. The chloroform extract of the fruiting body of AC (FCl3-Cl3, 77.4%, 77.6 mg) and the water extract of the fruiting body of AC (FW-Cl3, 23.5%, 23.6 mg) were obtained.

In Control 3, 100.9 mg lyophilized EEAC was fractionation with dichloromethane and water (100 ml each, 1:1 (v/v)) by liquid-liquid partition extraction according to the literature of Shen et al., 2003. The dichrolomethane extract of the fruiting body of AC (FCl2-Cl2, 76.2%, 76.9 mg) and the water extract of the fruiting body of AC (FW-Cl2, 23.3%, 23.5 mg) were obtained.

Please refer to Table 1, which illustrates the comparison of anti-leukemia activity of the above-mentioned extracts. In the present Embodiment 2, FEA exhibited the best activity that demonstrated the repeatability in production for concentrating cytotoxic components in EEAC. Comparing antiproliferative activity of FA with those in Control 1, FA (104.10 μg/ml) were more potent than FEA-EA (156.47 μg/ml) which prepared by the acceptable partition method in food science. Although the fractions (FCl3-Cl3 and FCl2-Cl2) had shown competitive antiproliferative activity referring to FEA, usage of those chlorine-containing organic solvents were limited or forbidden. Therefore, the methods in the prior art are not ideal preparation procedures.

TABLE 1

Antiproliferative activity of extracts in Embodiment 2 and the respective controls

|  | Product | Anti-leukemia activity ($IC_{50}$) (μg/ml) |
| --- | --- | --- |
| Embodiment2 | EEAC | 182.94 |
|  | FC | 156.36 |
|  | FA | 104.10 |
|  | FB | >200 |
| Control 1 | FEA-EA | 156.47 |
|  | FW-EA | >200 |
| Control 2 | FCl3-Cl3 | 126.04 |
|  | FW-Cl3 | >200 |
| Control 3 | FCl2-Cl2 | 115.03 |
|  | FW-Cl2 | >200 |

Experiment 2

NMR Analysis

The experimental conditions of $^1$H NMR spectrum in Experiment 2 were: the equipment with 400 MHz resolution; the concentration of 10.0 mg/0.75 ml; and EEAC, FC, EA, FB and zhankuic acid A were dissolved in $C_5D_5N$ solution.

Please refer to FIGS. 9(A) to 9(E), which respectively show $^1$H NMR spectra of (A) EEAC, (B) FC, (C) FA, (D) FB and (E) zhankuic acid A dissolved in $C_5D_5N$ at 400 MHz. The characteristic $^1$H NMR signals of zhankuic acid A showed two tertiary methyls [$\delta_H$ 0.70 ($H_3$-18) and 1.61 ($H_3$-19) (each 3H, s)], three secondary methyls [$\delta_H$ 0.89 (3H-21, d, J=5.6 Hz), 1.03 (3H-29, d, J=6.4 Hz), and 1.52 (3H-27, d, J=7.2 Hz)], and terminal olefinic protons ($H_2$-28) in 24-exo-methylene-26-oic acid side-chain at $\delta_H$ 5.08 (1H, br s) and 5.24 (1H, br s). When $^1$H NMR spectra in FIGS. 9(A) to 9(E) were partially aligned and compared with each other, $^1$H NMR spectra of EEAC and FA exhibited clearly these distinguishable signals in FIGS. 9(A) and 9(C), and this result was identical with that in FIGS. 3(A) and 3(B). Moreover, the signals of the methine protons [$\delta_H$ 3.01 (1H-12, d, J=13.6 Hz), 3.17 (1H-1, ddd, J=13.3, 6.8, 2.4 Hz), and 3.48 (1H-25, q, J=7.2 Hz)] of zhankuic acid A were also found circumspectly in $^1$H-NMR spectra of EEAC and FA. However, the above-mentioned specific signals were not observed at all in the $^1$H NMR spectra of FC and FB in FIGS. 9(B) and 9(D). Therefore, it can be identified that the major active component, zhankuic acid A, of the fruiting body of AC can be concentrated in ethyl acetate layer by the preparation method of the present invention.

Standard was isolated from 6.8 g FA. In addition to zhankuic acid A, another three major components, antcin C (formula II), zhankuic acid C (formula III) and dehydroeburicoic acid (formula IV), could be obtained and identified by NMR and ESIMS. The structural formulas, isolations and purifications of these three major active components were illustrated as follows.

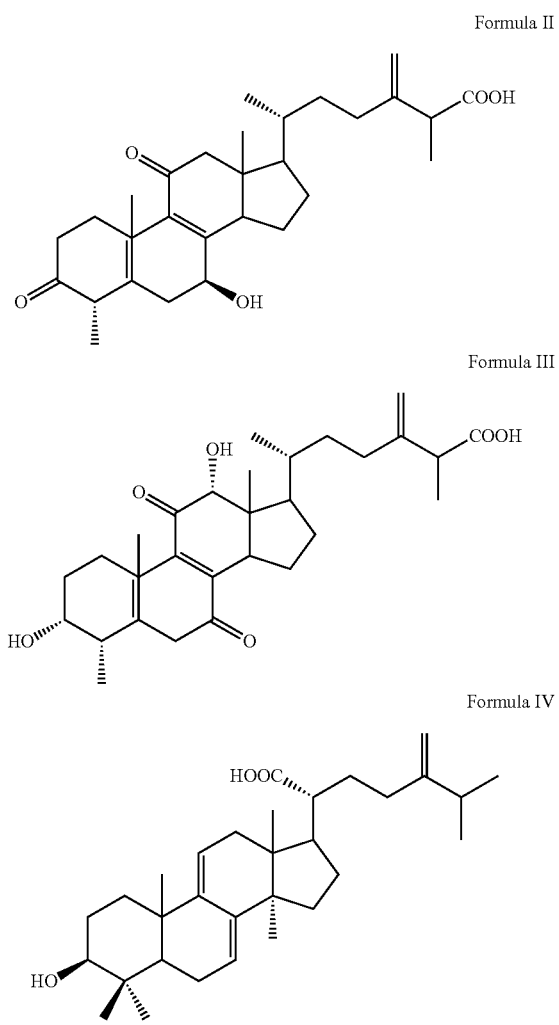

Formula II

Formula III

Formula IV (1) Isolation and purification of dehydroeburicoic acid: FA (6.8 g) was chromatographed with n-hexane-ethyl acetate-methanol (10:1:0, 5:1:0, 1:1:0, 0:1:0, 0:40:1, 0:30:1, 0:20:1 and 0:10:1 respectively) in silica gel 60 (Merck, 230-400 mesh) to obtain 17 fractions, wherein the fourth fraction (Fraction 4, 588.4 mg) was chromatographed with ethyl acetate-dichloromethane-methanol ($EA-CH_2Cl_2$-MeOH, 1:1:6) in Sephadex LH-20 to yield 3 sub-fractions. The first sub-fraction (Fraction 4-1, 568.6 mg) was further chromatographed with CHCl$_3$-MeOH (35:1) in Silica gel 60 to yield 3 another sub-fractions. Fifty milligrams (50 mg) from 240.3 mg of the second sub-fraction (Fraction 4-1-2) was purified with ODS HPLC column (250×10 mm, Hypersil®, methanol-water (90:10)) to obtain 10.3 mg dehydroeburicoic acid (R$_t$ 27 min, flow rate 2 ml/min).

(2) Isolation and purification of zhankuic acid A: The sixth fraction (Fraction 6, 970.9 mg) was chromatographed with EA-CH$_2$Cl$_2$-MeOH (1:1:6) in Sephadex LH-20 to yield sub-fractions. One hundred milligrams (100 mg) from 901.0 mg of the second sub-fraction (Fraction 6-2) was further chromatographed with ODS HPLC column (250×10 mm, Hypersil®, acetonitrile-water (75:25)) to obtain 77.5 mg of zhankuic acid A (R$_t$ 12 min, flow rate 2 ml/min).

(3) Isolation and purification of antcin C: The tenth fraction (Fraction 10, 132.6 mg) was chromatographed with CH$_2$Cl$_2$-MeOH (15:1) by preparative TLC to yield 5 sub-fractions. The second sub-fraction (Fraction 10-2, 85.0 mg) was purified with ODS HPLC column (250×10 mm, Hypersil®, acetonitrile-water (70:30)) to obtain 40.9 mg of antcin C (R$_t$ 10 min, flow speed 2 ml/min).

(4) Isolation and purification of zhankuic acid C: The thirteenth fraction (Fraction 13, 1.4 g) was chromatographed with CH$_2$Cl$_2$-MeOH (15:1) in Silica gel 60 to yield 7 sub-fractions. The fifth sub-fraction (Fraction 13-5, 107.5 mg) was purified with ODS HPLC column (250×10 mm, Hypersil®, acetonitrile-water (70:30)) to obtain 26.0 mg of zhankuic acid C (R$_t$ 10 min, flow rate 2 ml/min).

Experiment 3

HPLC Analysis

HPLC spectra of four obtained major active components and FA were compared. The HPLC conditions were provided as follows. HPLC was Shimadzu LC-10AT, the detector was Shimadzu SPD-M10A photodiode array detector, the auto sampler was Shimadzu SIL-20A prominence auto sampler; the HPLC column was Cosmosil 5C-18-MS-II (250×4.6 mm), solvent A in mobile phase was acetonitrile and solvent B was water (in 0.1% acetic acid), flow rate was 1 ml/min, column temperature was room temperature, and detection wavelength was 254 nm and 270 nm.

The parameters of solvent system were illustrated as follows. Mobile phase included solvent A and B, linear gratitude was operated at 0 to 30 minutes (45% A to 50% A), 30 to 35 minutes (50% A to 55% A), 35 to 45 minutes (55% A to 60% A), 45 to 55 minutes (60% A to 70% A), 55 to 60 minutes (70% A to 85% A) and 60 to 100 minutes (85% A to 100% A). Flow rate and column temperature were illustrated as above.

In accordance with the published literatures (Chen et al., 1995; Cherng et al., 1995; Hsu et al., 2007; Shen et al., 2003), zhankuic acid A, antcin C and zhankuic acid C are stereo isomers having the chiral center at C-25 position, but they cannot be purified at the isolation procedures. However, two stereo isomers can be separated and observed, i.e. two peaks represented on the chromatographic spectrum, at the above-mentioned HPLC conditions.

Figure 10A:
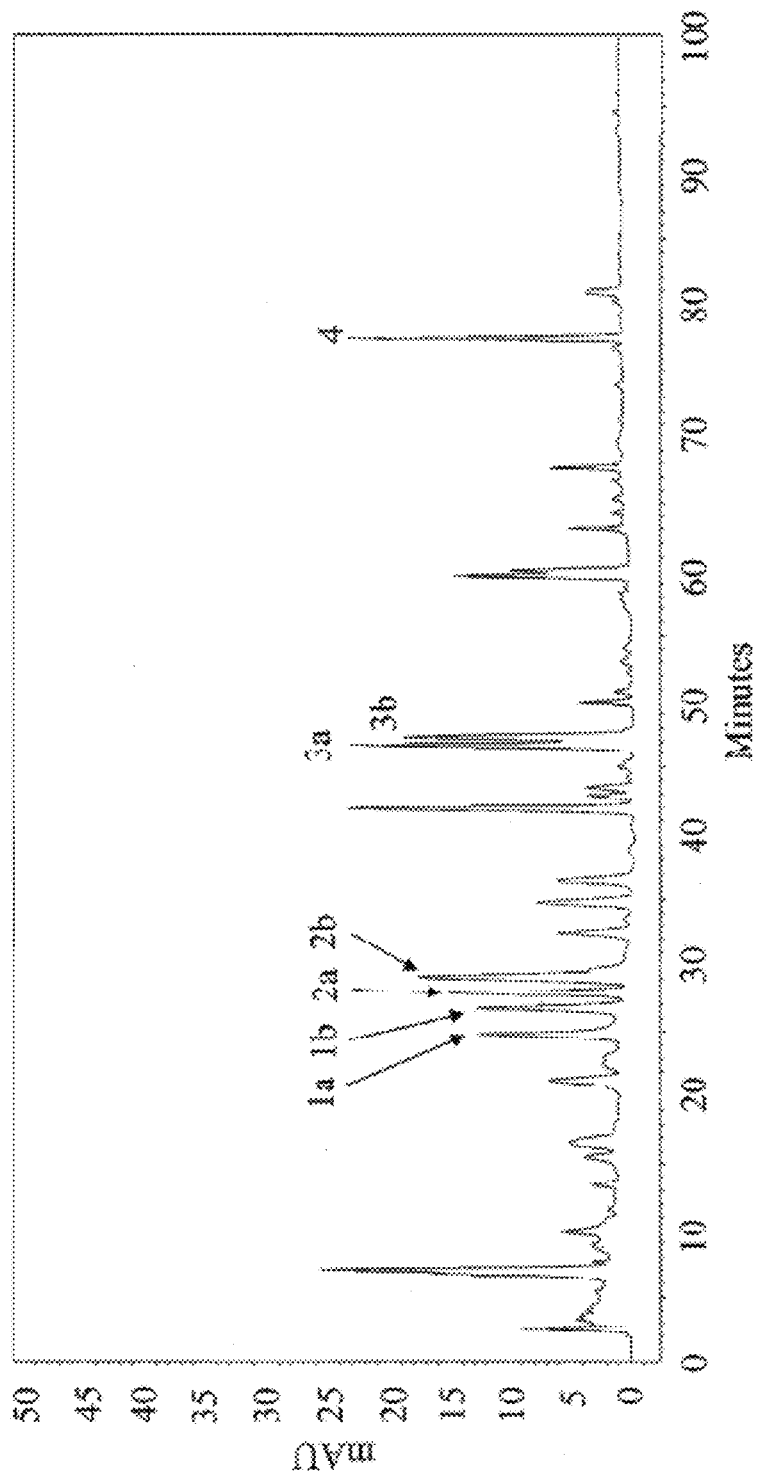
FIGS. 10(A) and 10(B) respectively show HPLC profiles of FA at (A) 254 nm and (B) 270 nm.

Please refer to FIG. 10(A) and Table 2, which show comparisons of peak area and height for the respective components in FA after with HPLC at 254 nm wavelength. In Table 2, zhankuic acid A represented two peaks at 254 nm wavelength and retention time of 46.739 and 47.347 min, and the determined area occupied 16.26% and the determined height occupied 17.27% of the total active layer. Zhankuic acid A had the highest area and height in four major active components.

TABLE 2

Comparisons of peak area and height for the respective components in FA after with HPLC at 254 nm wavelength

| Product | Peak number | Retention time (min) | Area (%) | Height (%) |
| --- | --- | --- | --- | --- |
| Antcin C | 1a | 24.779 | 6.27 | 4.84 |
| Antcin C | 1b | 26.734 | 5.70 | 4.90 |
| Zhankuic acid C | 2a | 27.933 | 6.48 | 5.87 |
| Zhankuic acid C | 2b | 29.140 | 8.37 | 6.96 |
| Zhankuic acid A | 3a | 46.739 | 8.97 | 9.51 |
| Zhankuic acid A | 3b | 47.347 | 7.29 | 7.76 |
| Dehydroeburicoic acid | 4 | 77.531 | 6.24 | 9.22 |
| Others | | | 50.68 | 50.94 |
| Total | | | 100.00 | 100.00 |

Figure 10B:
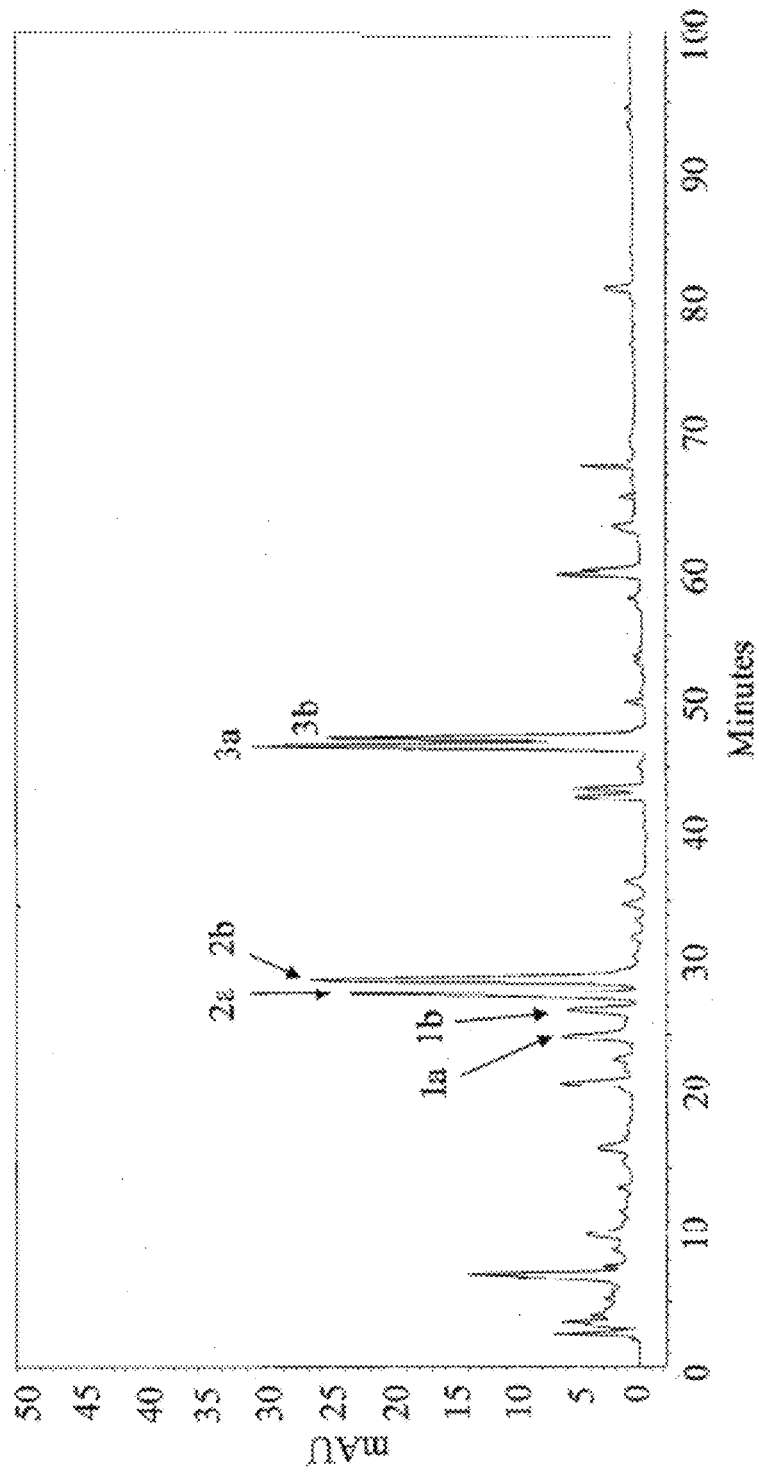

Please refer to FIG. 10(B) and Table 3, which shows comparisons of peak area and height of the respective components in FA with HPLC at 270 nm wavelength. In Table 3, zhankuic acid A represented two peaks at 270 nm wavelength and retention time of 46.736 and 47.352 min, and the determined area occupied 26.53% and the determined height occupied 27.86% of the total active layer. Zhankuic acid A also had the highest peak height in four major active components.

TABLE 3

Comparisons of peak area and height of the respective components in FA with HPLC at 270 nm wavelength

| Product | Peak number | Retention time (min) | Area (%) | Height (%) |
| --- | --- | --- | --- | --- |
| Antcin C | 1a | 24.761 | 5.42 | 3.49 |
| Antcin C | 1b | 26.719 | 4.07 | 3.27 |
| Zhankuic acid C | 2a | 27.931 | 12.86 | 11.47 |
| Zhankuic acid C | 2b | 29.147 | 16.38 | 12.80 |
| Zhankuic acid A | 3a | 46.736 | 14.53 | 15.43 |
| Zhankuic acid A | 3b | 47.352 | 12.00 | 12.43 |
| Others | | | 34.74 | 41.11 |
| Total | | | 100.00 | 100.00 |

From the results of NMR and HPLC analysis, it can be known that zhankuic acid A is the major active component in EEAC, and antcin C, zhankuic acid C and dehydroeburicoic acid are another ones. FA is defined as the triterpenoids-rich fraction and shows antiproliferative activity in HL 60 cells. Accordingly, the above-mentioned experimental method can be the power tool for detecting the components of triterpenoids of A. camphorata in the industry.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method for measuring an existence and an amount of at least one triterpenoid of a fruiting body of an *Antrodia camphorata*, comprising steps of:
   (a) extracting the fruiting body with a first ethanol solution to obtain an ethanol extract;
   (b) extracting the ethanol extract with an n-hexane to obtain an n-hexane extract and a first residue;
   (c) extracting the first residue with an ethyl acetate to obtain an ethyl acetate extract and a second residue;
   (d) extracting the second residue with a second ethanol solution to obtain a second ethanol extract; and
   (e) measuring the existence and the amount, by using a nuclear magnetic resonance and a high performance liquid chromatography respectively, of the at least one triterpenoid in the n-hexane extract, the ethyl acetate extract and the second ethanol extract, wherein the at least one triterpenoid being one selected from a group consisting of a zhankuic acid A, a dehydroeburicoic acid, an actcin C and a zhankuic acid C is only presented in the ethyl acetate extract among the n-hexane extract, the ethyl acetate extract and the second ethanol extract.

2. The method according to claim 1, wherein the existence of the at least one triterpenoid is performed by a $^1$H-nuclear magnetic resonance ($^1$H-NMR) at a resolution of at least 200 MHz, and the ethyl acetate extract is dissolved in one of a deuterium chloroform ($CDCl_3$) and a pyridine-D5 ($C_5D_5N$).

3. The method according to claim 1 further comprising a step (c1) of sequentially isolating the ethyl acetate extract with a first trichloromethane-methanol ($CHCl_3$-MeOH) solution with a first ratio of 1:3 and a second $CHCl_3$-MeOH solution with a second ratio of 25:1 to obtain the zhankuic acid A.

4. The method according to claim 1 further comprises a step (c1) of chromatographing the ethyl acetate extract with a plurality of n-hexane-ethyl acetate-methanol (n-hexane-EA-MeOH) solutions to sequentially obtain at least four fractions having a first fraction, a second fraction, a third fraction and a fourth fraction.

5. The method according to claim 4 further comprising steps of:
   chromatographing the first fraction with a first ethyl acetate-dichloromethane-methanol (EA-$CH_2Cl_2$-MeOH) solution to obtain a first sub-fraction; and
   chromatographing the first sub-fraction with a trichloromethane-methanol ($CHCl_3$-MeOH) solution with a ratio of 35:1 to obtain the dehydroeburicoic acid.

6. The method according to claim 4 further comprising a step of chromatographing the second fraction with a second ethyl acetate-dichloromethane-methanol (EA-$CH_2Cl_2$-MeOH) solution to obtain the zhankuic acid A.

7. The method according to claim 4 further comprising a step of chromatographing the third fraction with a dichloromethane-methanol ($CH_2Cl_2$-MeOH) solution with a ratio of 15:1 to obtain the antcin C.

8. The method according to claim 4 further comprising a step of chromatographing the fourth fraction with a dichloromethane-methanol ($CH_2Cl_2$-MeOH) solution with a ratio of 15:1 to obtain the zhankuic acid C.

9. A method for measuring an existence and an amount of triterpenoid in a target object, comprising steps of:
   (a) extracting the target object with a first ethanol solution to obtain an ethanol extract, wherein the target object is a fruiting body of an *Antrodia camphorate*;
   (b) sequentially extracting the ethanol extract with an n-hexane and an ethyl acetate to obtain an ethyl acetate extract; and
   (c) measuring the existence and the amount of the triterpenoid in the ethyl acetate extract, wherein the triterpendoid is only present in the ethyl acetate extract.

10. The method according to claim 9, wherein in the step (c), the existence of the triterpenoid is performed by a nuclear magnetic resonance at a resolution of at least 200 MHz, the ethyl acetate extract is dissolved in a pyridine-D5 ($C_5D_5N$), and the amount of the triterpenoid is performed by a high performance liquid chromatography (HPLC).

11. An extracting method of at least one triterpenoid in a triterpenoid-concentrating fraction from a fruiting body of an *Antrodia camphorata*, comprising steps of:
   (a) extracting the fruiting body with a first ethanol solution to form a first ethanol extract; and
   (b) sequentially extracting the first ethanol extract with a plurality of organic solvents to obtain a plurality of organic solvent extracts, wherein each of the plurality of organic solvents has a polarity and the step (b) has an extracting sequence such that the polarity of a specific one of the plurality of organic solvents is higher than that of the preceding one of the specific organic solvent, and the triterpenoid-concentrating fraction is only presented in a specific one of the plurality of organic solvent extracts, wherein the plurality of organic solvents are an n-hexane to obtain an n-hexane extract, an ethyl acetate to obtain an ethyl acetate extract, and a second ethanol to obtain a second ethanol extract, and the at least one triterpenoid being one selected from a group consisting of a zhankuic acid A, a dehydroeburicoic acid, an actcin C and a zhankuic acid C is only presented in the ethyl acetate extract among the n-hexane extract, the ethyl acetate extract and the second ethanol extract.

12. The method according to claim 11, wherein the fruiting body is ground before the step (a).

13. The method according to claim 11, wherein the step (b) further comprises steps of:
- (b11) extracting the first ethanol extract with an n-hexane to obtain an n-hexane extract and a first residue;
- (b12) extracting the first residue with an ethyl acetate to obtain an ethyl acetate extract and a second residue; and
- (b13) extracting the second residue with a second ethanol solution to obtain a second ethanol extract.

14. The method according to claim 13, wherein the step (b12) further comprises a step (b121) of isolating the ethyl acetate extract with a plurality of trichloromethane-methanols to obtain a zhankuic acid A, wherein the plurality of trichloromethane-methanols have respective ratios of a trichloromethane to a methanol.

15. The method according to claim 13, wherein the step (b12) further comprises a step (b121) of isolating the ethyl acetate extract with a plurality of n-hexane-ethyl acetate-methanols to obtain a plurality of fractions of the ethyl acetate extract, wherein the plurality of n-hexane-ethyl acetate-methanols have respective ratios of an n-hexane-ethyl acetate to a methanol.

16. The method according to claim 15, wherein the step (b121) further comprises at least one step of:
- (b121-1) sequentially isolating a first one of the plurality of fractions with an ethyl acetate-dichloromethane-methanol, a trichloromethane-methanol and a methanol-water to obtain a dehydroeburicoic acid;
- (b121-2) sequentially isolating a second one of the plurality of fractions with the ethyl acetate-dichloromethane-methanol and an acetonitrile-water having a first ratio of an acetonitrile to a water to obtain a zhankuic acid A;
- (b121-3) sequentially isolating a third one of the plurality of fractions with a dichloromethane-methanol and the acetonitrile-water having a second ratio of an acetonitrile to a water to obtain an actcin C; and
- (b121-4) sequentially isolating a fourth one of the plurality of fractions with the dichloromethane-methanol and the acetonitrile-water having a third ratio of an acetonitrile to a water to obtain a zhankuic acid C.

17. The method according to claim 11, wherein the step (a) further generates a residue, and the method further comprises a step (a1) of extracting the residue with a water to obtain a water extract.

* * * * *